United States Patent [19]

Pirkle, Jr. et al.

[11] Patent Number: 4,536,380

[45] Date of Patent: Aug. 20, 1985

[54] PROCESS FOR CONDUCTING REACTIONS USING A CIRCULATING MAGNETICALLY STABILIZED BED TO CONTROL REACTION TEMPERATURE PROFILE

[75] Inventors: James C. Pirkle, Jr., Lebanon; Angelo A. Montagna, Summit; Philip A. Ruziska, Chester, all of N.J.

[73] Assignee: Exxon Research and Engineering Co., Florham Park, N.J.

[21] Appl. No.: 449,996

[22] Filed: Dec. 15, 1982

[51] Int. Cl.³ .................... C01C 1/04; C07D 301/22
[52] U.S. Cl. ................................. 423/359; 549/535
[58] Field of Search ................ 549/535; 423/359-363

[56] References Cited

U.S. PATENT DOCUMENTS

| | | | |
|---|---|---|---|
| 2,430,443 | 11/1947 | Becker | 549/535 |
| 2,519,481 | 8/1950 | Kubie et al. | 23/1 |
| 2,550,389 | 4/1951 | Souby et al. | 23/198 |
| 2,769,771 | 11/1956 | Griffin, Jr. | 549/535 |
| 2,853,371 | 9/1958 | Christensen et al. | 23/289 |
| 3,305,312 | 2/1967 | Weinstein et al. | 23/199 |
| 3,368,956 | 2/1968 | Yeh | 204/177 |
| 3,480,393 | 11/1969 | Stark et al. | 23/199 |
| 3,531,246 | 9/1970 | Matsen | 23/199 |
| 3,653,831 | 4/1972 | Burnett | 23/199 |
| 3,839,229 | 10/1974 | Senes et al. | 252/455 R |
| 4,115,927 | 9/1978 | Rosenweig | 34/1 |
| 4,130,570 | 12/1978 | Boreskov et al. | 260/348.35 |
| 4,132,005 | 1/1979 | Coulaloglou et al. | 34/10 |
| 4,148,866 | 4/1979 | Becker | 423/359 |
| 4,153,673 | 5/1979 | Becker | 423/359 |
| 4,197,418 | 4/1980 | Lee et al. | 585/469 |
| 4,242,317 | 12/1980 | Pinto | 423/359 |
| 4,247,987 | 2/1981 | Coulaloglou et al. | 34/1 |
| 4,283,204 | 8/1981 | Savage et al. | 55/3 |

FOREIGN PATENT DOCUMENTS

| | | |
|---|---|---|
| 16090 | 11/1975 | Bulgaria . |
| 16510 | 6/1976 | Bulgaria . |
| 2237188 | 2/1973 | Fed. Rep. of Germany ...... 549/535 |
| 855091 | 11/1960 | United Kingdom ................ 549/535 |
| 1019235 | 2/1966 | United Kingdom . |
| 1019236 | 2/1966 | United Kingdom . |

OTHER PUBLICATIONS

McCabe, W. L., et al., Unit Operations of Chemical Engineering, McGraw Hill, pp. 301 to 303, 517 to 539, (1967).

Zrenchev et al., Khimiya I. Industriya, 51, pp. 256-258, (1979), (translation only).

A. E. McIlhinney et al., Can. J. Chem. Eng., 42, #5, pp. 232-233 (Oct. 1964), (abstract only).

J. Wasilewski et al., Chem. Tech. (Berlin), 17, #2, pp. 83-86, (Feb. 1965), (abstract only).

McIlhinney A. E., et al., "Silver Sprayed Cylindrical Mesh Packing in a Fluidized Bed", Can J Chem Eng., 42, Oct. 1964, (abstract).

Wasilowski J., et al., "Fluidized Bed Catalytic Oxidation of Ethylene to Ethylene Oxide", Chem Tech, 17, Feb. 1965, (abstract).

Primary Examiner—L. Dewayne Rutledge
Assistant Examiner—Christopher W. Brody
Attorney, Agent, or Firm—Janet E. Hasak; E. Thomas Wheelock

[57] ABSTRACT

An endothermic or exothermic chemical reaction may be conducted whereby a flowable bed of magnetizable particles such as catalytic particles is subjected to an applied magnetic field, a reaction fluid is circulated through the bed under conditions so as to effect an exothermic or endothermic reaction, the bed of particles is circulated at a rate such that the temperature profile of the bed and reaction fluid throughout their entire contact in a reactor is at or about the temperature profile which results in maximization, at each point along the reactor, of at least one of: conversion, selectivity or product yield, and the desired reaction product is recovered.

In a preferred embodiment the solids are transported countercurrently to the reaction fluid in the synthesis of ammonia. In another preferred embodiment the solids are transported cocurrently with the reaction fluid in the synthesis of ethylene oxide.

16 Claims, 8 Drawing Figures

Temperature Controlled Magnetically
Stabilized Fluid Bed Reactor for
Ammonia Synthesis Stagewise Four Bed Reactor with Inter Bed Quench for
Ammonia Synthesis (As Control)

Magnetically Stabilized Fluid Bed For
Epoxide Synthesis

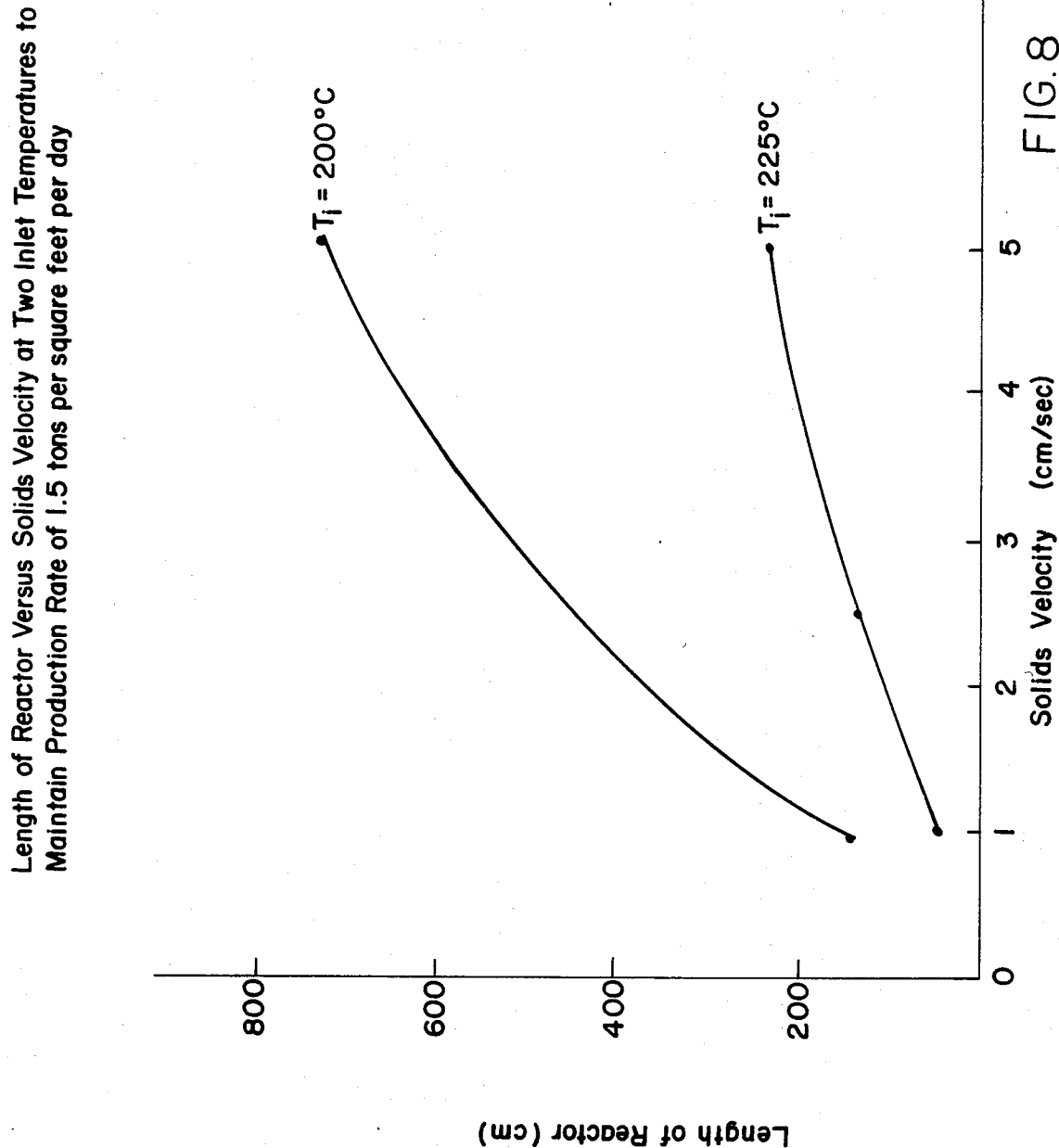

PROCESS FOR CONDUCTING REACTIONS USING A CIRCULATING MAGNETICALLY STABILIZED BED TO CONTROL REACTION TEMPERATURE PROFILE

BACKGROUND OF THE INVENTION

1. Field of the Invention

This invention relates to a process for carrying out an endothermic or exothermic reaction using a moving bed of magnetically stabilized particles wherein the reaction temperature profile is controlled to an optimum level for maximum product yield, selectively and/or conversion. This invention is particularly suited to reaction processes constrained by equilibrium limitations, such as synthesis of ammonia or methanol, and to reaction processes where it is important to limit maximum reactor temperature to avoid producing undesirable by-products, such as epoxidation of ethylene.

2. Description of Related Disclosures

Conversion of hydrogen and nitrogen to ammonia generally occurs in the presence of a promoted iron catalyst at temperatures between about 343° C. and 538° C. As the reaction is exothermic, releasing about 23,000 Btu per pound-mole of ammonia produced, the heat generated in the catalyst bed must be removed by some means to control bed temperatures and provide an optimum temperature profile for efficient catalyst utilization.

In designing reactors for the synthesis of ammonia, several factors must be considered. High pressure is required to shift the reaction equilibrium significantly toward conversion to ammonia. Also, lower temperatures favor higher equilibrium concentrations of ammonia at a given pressure, but excessively low temperatures are associated with slow kinetic rates of reaction. Therefore, the optimal temperatures profile associated with the reaction which maximizes conversion to ammonia for a given inlet gas pressure, temperature and composition is a compromise between adequate equilibrium concentration of ammonia and a suitably rapid rate of reaction.

Many of the present commercial reactors for synthesis of ammonia from hydrogen and nitrogen constitute fixed bed reactors, which suffer from at least two limitations. First, large catalyst particles, which reduce surface area per unit reactor volume and which retard the reaction rate, must be employed to prevent the pressure drop across the bed from being prohibitively large. Secondly, the optimal temperature profile which maximizes conversion in the reactor is difficult to achieve. Conventional reactor designs attempting to approximate the optimal temperature profile include adiabatic beds in series with quenches between the beds, adiabatic beds in series with heat exchangers between the beds, and use of catalyst beds with cooling tubes installed within the bed. However, the effectiveness of interstage quenching and cooling (as takes place in a multiple adiabatic bed design) is limited by the significant temperature rise which occurs, resulting in the operation of a major portion of the catalytic volume at a temperature far from the optimum reaction temperature for conversion. While the use of cooling tubes in the bed itself can, theoretically, provide a closer approach to the optimum reaction temperature profile, the cooling surface to catalyst volume ratio is fixed by the design and it is not possible to make adjustments for different operating conditions and catalyst activity so as to maintain an optimum reaction temperature profile throughout the life of the catalyst charge.

The use of conventional stationary fluidized beds without magnetic stabilization for ammonia synthesis allows for smaller particles to be used while avoiding any large pressure drops but does not permit an optimal temperature profile to be attained for maximum conversion.

In other exothermic reactions such as partial oxidation of hydrocarbons, optimum temperature profiles are important when unacceptable side reactions such as combustion occur at high temperatures so as to affect adversely the selectivity for the desired product. Thus, for example, it has been found that the conversion of ethylene to ethylene oxide using a fixed silver catalyst bed is limited to about 20-25% to obtain acceptable selectivity (at least about 70%) to ethylene oxide. This necessitates substantial recycling of the unconverted ethylene. Attempts to achieve higher conversions result in releasing more heat and lowering the selectivity because higher temperatures favor complete oxidation of ethylene to carbon dioxide and water. Present technology utilizes complicated cooling systems such as shell and tube type heat exchangers to control the reaction temperature of the fixed bed reactor. However, selectivity is limited to about 70% and conversion per pass is limited to 20-25% of the ethylene feed. Recycling the unreacted ethylene requires cool-down and recompression, and "hot spots" due to fluid "dead spaces" in the cooling medium and shell-and-tube type heat exchangers are often problematical with respect to temperature runaway. Heat transfer also presents a problem in the synthesis of hydrocarbons from carbon monoxide and hydrogen.

Numerous workers have studied the influence of magnetization on the dynamics of fluidized solids in batch beds. An early account of this phenomenon was reported by M. V. Filippov, Applied Magnetohydrodynamics, *Trudy Instituta Fizika Akad. Nauk.*, Latviiskoi SSR 12, 215 (1960). Subsequent workers have observed the influence which magnetization exerts on pulsations, heat transfer, structure and other characteristics of magnetized and fluidized solids in batch beds. A review of some of this work is provided by Bologa and Syutkin, *Elektron Obrab Mater*, 1, 37 (1977). In particular, a report of the effect of electromagnetic fields on the heat transfer process between the heating surface and the fluidized bed is given by S. V. Syutkin et al., *Elektron Obrab Mater*, 6, 61 (1976). In addition, studies of the effect of macrokinetics on the value of optimal temperatures were made in a fluidal layer of catalyst by the flow method in the synthesis of ammonia and methanol by I. A. Zrenchev, *Dokl. Bolg. Akad. Nauk*, 27, 1501 (1974). Invanov and coworkers have described some benefits of using an applied magnetic field on a stationary bed of fluidized ferromagnetic solids in the synthesis of ammonia and some of the characteristics of the bed for this process. See U.K. Pat. No. 1,148,513 and numerous publications by the same authors, e.g., Ivanov et al., *Intern. Chem. Eng.*, 15, 557 (1975), Ivanov et al., *Dokl. Bolg. Akad. Nauk*, 28, 55 (1975) and Ivanov et al., *Dolk. Bolg. Akad. Nauk*, 22, 1405 (1969), which report that the use of the magnetic field restricts carryover of catalyst particles to the effluent gas stream. In addition, I. Zrenchev et al., *Khim. I. Industriya*, 51, 256 (1979) relates to ammonia synthesis in a fixed bed in the presence of a magnetic field. The use of magnetically stabilized fluidized beds in general and the use thereof in a plurality of chemical reactions, separations and other applications are disclosed in U.S. Pat. No. 4,115,927. Additionally, a method for controlling temperatures of exothermic reactions using a magnetic field is described in U.S. Pat. No. 2,519,481.

U.S. Pat. Nos. 4,247,987 and 4,283,204 describe the use of a magnetically stabilized bed to facilitate circulating solids countercurrently to the fluidizing medium whereby the solids and gases flow countercurrently to each other in plug-flow fashion. The disclosed applications of these concepts are in the recovery of solids from the main reaction or adsorption zone, the transfer of the solids to a regeneration zone and the clean-up of the solids prior to return to the main reaction or adsorption zone.

SUMMARY OF THE INVENTION

The present invention is directed to an improved process for conducting an endothermic or exothermic chemical reaction under fluidization conditions in a reactor, which comprises:

(a) subjecting a flowable bed containing magnetizable particles to an applied magnetic field having a substantial component along the direction of the external force field within the bed;

(b) passing a reaction fluid through the reactor in a plug-flow manner at a rate such that the fluid exerts pressure against and levitates the particles in the bed and under conditions such that an endothermic or exothermic reaction takes place in the presence of the bed;

(c) circulating the bed of particles through the reactor in a plug-flow manner and after its exit from the reactor recirculating the bed to the reactor, the circulating and recirculating of the bed being conducted at a rate such that the temperature profile of the bed and reaction fluid throughout their entire contact is at or about the temperature profile which results in maximization, at each position in the reactor, of at least one of the following: conversion, selectivity or product yield; and (d) recovering a reaction product.

Before recovery of the product the bed of particles may be regenerated as needed.

The process herein may be used to conduct any endothermic or exothermic heterogeneous or homogeneous chemical reaction whenever control of the temperature throughout the reaction is required or desired. In a preferred embodiment herein the particles employed in the flowable bed are catalytic materials and the reaction is exothermic. This invention is particularly useful for the synthesis of ammonia, methanol, sulfuric acid or hydrocarbons, or for partial oxidation of hydrocarbons such as ethylene.

In the synthesis of ammonia, at the optimum temperature profile, less catalyst volume is required to obtain the same level of conversion (i.e., yield of product) as obtained using a conventional fixed bed reactor design, and a higher equilibrium concentration can be expected than is possible using a conventional fixed bed or fluidized bed reactor design. In addition, the reactor can be operated under conditions which obviate the need for external heating or cooling of the solid catalyst upon recirculation or the need for internal heat exchangers. Moreover, the process herein, improving the utilization of catalyst, permits increased ammonia production and reduced circulation rate or lower synthesis loop pressures than are possible with conventional reactor designs, thereby allowing for a considerable reduction in energy for ammonia production.

In the synthesis of ethylene oxide, the process herein provides selectivities of up to 80–85% when the solids flow rates are sufficiently high to minimize the longitudinal temperature profile by providing extra heat capacity. Additionally, the process scheme involves minimal or no ethylene recycling.

BRIEF DESCRIPTION OF THE DRAWINGS

FIG. 3 also graphically illustrates the mole percentage of ammonia in the reaction fluid and the optimum reaction temperature of the gas phase as a function of the axial position in the reactor.

FIG. 8 represents a graphical illustration of the length of the reactor as a function of solids velocity at two inlet temperatures required to maintain an ethylene oxide production rate of 1.5 tons per square feet per day.

DESCRIPTION OF THE PREFERRED EMBODIMENTS

This invention applies to those chemical reactions which can be classified as exothermic or endothermic. The term "exothermic" is used herein to describe those reactions from which heat is evolved in the course thereof, such as in the synthesis of ammonia, methanol, sulfuric acid, or hydrocarbons and the epoxidation of ethylene. The term "endothermic" refers to those reactions wherein heat is consumed as the reaction proceeds. Both types of reactions would necessitate a form of temperature control.

Figure 1:
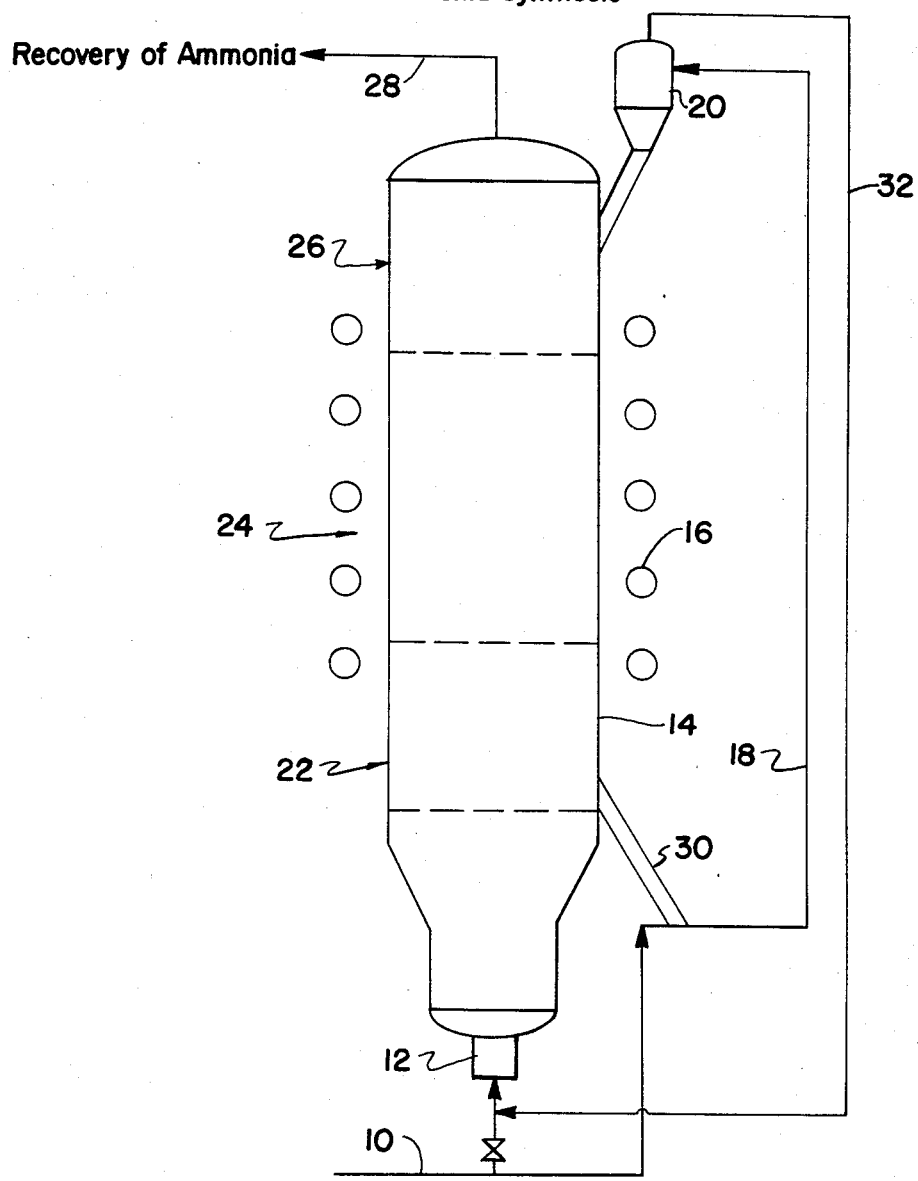
FIG. 1 represents a schematic flow diagram of a preferred ammonia synthesis process utilizing a temperature-controlled counter-current magnetically stabilized bed catalytic reactor and controlled circulation of solids and feed gas.
Figure 5:
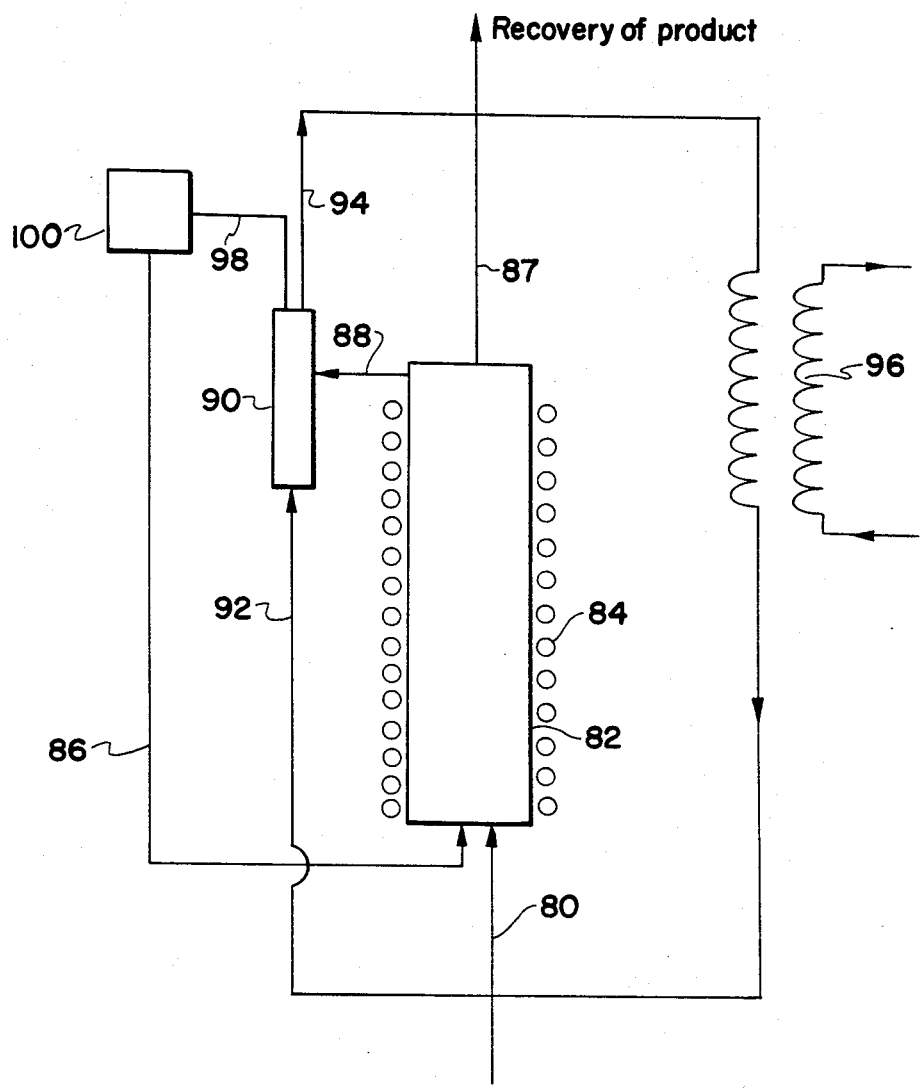
FIG. 5 represents a schematic flow diagram of a preferred epoxidation process utilizing a magnetically stabilized bed catalytic reactor and circulation of solids and feed gas.

The reactor employed in the present invention may be described as basically one which is equipped with a gas inlet and a gas outlet port at essentially opposite ends of the reactor, a solids inlet and a solids outlet port at essentially opposite ends of the reactor, and means for subjecting the particles in the reactor bed to a magnetic field such as electrical coils located along the entire length of the reactor. The exact reactor design applicable for a particular reaction will vary with the type of reaction, but representative vertical reactors are depicted in FIGS. 1 and 5 for ammonia and ethylene oxide production, respectively.

In the process herein fluidization conditions are achieved when the magnetizable solid particles in the reactor are subjected to a magnetic field, preferably a uniformly applied magnetic field, having a substantial component along the direction of the external force field (e.g., gravity) such that the magnetizable particles will have a component of magnetization along the direction of the external force field. The magnetization of the magnetizable particles should not be sufficient to cause substantial particle-to-particle agglomeration as this will decrease the overall fluidity of the bed particles. Preferably, the strength of the magnetic field and its deviation from a vertical orientation are maintained so as to prevent and/or suppress the formation of bubbles in the fluidized bed at a given reaction fluid flow rate and with a selected fluidized particles composition.

The particles employed in the process herein may be defined as any which are capable of magnetization. Such particles may function as catalysts for the reaction taking place, as in a heterogeneous reaction, but this is not necessary, and the particles may merely be present to provide heat capacity or act as a heat sink to cause the reaction of reactant fluids to be conducted at close to or at the optimum temperature profile for product yield, as in a homogeneous reaction. Representative of suitable particles herein are solids which contain inclusions of smaller particles such as iron or stainless steel or particles coated with a magnetizable metal. Iron or promoted iron particles are particularly suited as catalysts for ammonia and hydrocarbon synthesis, and silver-coated particles may be employed for ethylene oxide production.

In general, the size of the particles in the fluidized bed will range from about 150 to 300 microns in diameter. If the particles are too small they will not support a sufficiently high throughput of reaction fluid. On the other hand, if the particles are much larger, the reaction is less effective, at least for the ammonia synthesis reaction. The density of the particles must be fairly large and depends on the magnetic field strength.

The reaction fluid employed in the process of this invention may be defined as any gas or liquid reactant or any mixture of gases and/or liquids comprising, before contact with the particles, at least one gaseous or liquid component which is to be reacted in the reaction. Typically the reaction fluid will comprise two or more chemical reactants which are kept in contact throughout the reaction. It will be understood by this definition that during the course of the reaction the reaction fluid will change in relative proportions of components as the reactants are consumed and as the product comprises an increasingly larger percentage of the total reaction fluid. As an example, in ammonia synthesis a mixture of hydrogen and nitrogen gases, optionally with a small amount of ammonia, will generally comprise the reaction fluid initially (i.e., before contact with the iron catalytic particles). During contact with the particles the reaction fluid will contain an increased amount of ammonia which will increase further in proportion to the reactants as the reaction proceeds. In ethylene oxide production ethylene and oxygen will comprise the reaction fluid, preferably in conjunction with an inert carrier gas such as nitrogen, until contact with the silver-coated particles, when the reaction fluid will additionally begin to contain the desired product ethylene oxide.

In the process herein, the reaction fluid is passed through the magnetized bed of particles in the reactor in a plug-flow manner at a rate which allows the fluid to exert a force against the bed, thereby levitating the particles in the particle bed. As the reaction fluid is passed through the bed of particles, the bed itself is moving through the reactor in a plug-flow manner. On exiting the reactor the particles are recirculated to the reactor (usually to an end opposite to that end from which it left the reactor) to be contacted again with the reaction fluid. Both the movements of reaction fluid and particles are conducted under conditions such that an endothermic or exothermic reaction will take place in the presence of the bed, e.g., using the proper reactor length, size of particles and inlet temperatures and pressures.

By "plug-flow" is meant that both reaction fluid and solids are transported such that negligible recirculation along the axis of flow takes place, in contrast to a conventional non-magnetically stabilized fluidized bed where the entire bed is in a high state of agitation and acts as a fully mixed vessel. Plug-flow allows for more efficient transfer of heat between the reaction fluid phase and the solids phase as the phases are transported along the length of the reactor than the conventional fluidized bed.

There are at least two ways in which the solid particles may be transported through the reaction apparatus relative to the reaction fluid. In one, which is particularly suited for the ammonia synthesis reaction, the solids are circulated countercurrently to the direction of flow of the reaction fluid (each flows in an opposite direction). For certain oxidation reactions (e.g., synthesis of maleic anhydride from butane) where it is necessary to minimize the number of "hot fronts" (zones of maximum temperature), countercurrent operations are desirable. In the other method, the solids are passed concurrently with the direction of flow of the reaction fluid (both flow in the same direction), as in the case of the epoxidation reaction. The solids which flow cocurrently provide sufficient heat capacity to maintain the temperature below a maximum for best selectivity, even when the conversion level approaches 70 to 90% where additional heat is released.

Some reactions, such as hydrocarbon synthesis, can be carried out by either a cocurrent or countercurrent operation. In the synthesis of hydrocarbons, use of a cocurrent bed is, however, preferred.

As used herein, the term "temperature profile" is defined as the separate temperatures of the solid and reaction fluid phases at each point or position along the length of the reaction apparatus. When a maximum temperature profile is specified, the temperature of neither phase is to exceed the maximum. The temperature profile can be expressed as a plot of the temperatures of each phase in the reactor as a function of the axial position of each phase in the reactor.

The temperature profile for a given reaction is maintained, using the process herein, at or about at an optimum temperature profile, i.e., that profile which will result in maximizing, at each position in the reactor, at least one of the following: conversion, product yield or selectivity. Conversion reflects the relative amounts of reactants which are converted to products by the reaction; product yield represents the actual amount of product obtained relative to the theoretical amount which would be obtained if all of the reactants had reacted stoichiometrically; and selectivity measures the preference of the reaction for a given product. It will be understood herein that using the least amount of catalyst volume to obtain a given product yield (i.e., minimizing catalyst volume, thus providing the most efficient utilization of catalyst) is equivalent to maximizing the yield of product. In the ammonia synthesis reaction it is most desirable to maximize product yield, which is the same as maximizing conversion. In the epoxidation of ethylene it is most important to maximize selectivity and conversion, which will result in maximum yield of ethylene oxide. Thus, for epoxidation the conversion should be greater than 20% and the selectivity greater than 75%.

The optimal temperature profile for a given reaction will obviously vary greatly with the type of reaction. For example, the optimum profile will depend on which of the above factors is to be maximized, whether countercurrent or cocurrent operations are employed, and whether the reactions are endothermic or exothermic. In general, however, the temperature profile is controlled so that it is continuously rising or falling during the reaction. When the operation is cocurrent and the reaction is exothermic, the temperature profile, to maximize selectivity, conversion and yield, will be controlled so as to rise. Thus, the temperature will range from the lowest temperature at which the catalyst is active, near or at the inlet portion of the reactor, to a temperature, near or at the outlet, which will not exceed a level which adversely affects the catalyst activity or induces by-product formation or complete oxidation. The exact temperature which should not be exceeded will depend on the type of reaction and the catalyst, but generally, for ethylene oxide synthesis, the temperature profile is preferably maintained below about 277° C. to achieve greater than 75% selectivity. For hydrocarbon synthesis via a cocurrent operation, the temperature profile is preferably maintained below about 350° C. if a promoted iron catalyst is employed. When the operation is cocurrent and the reaction is endothermic, the temperature profile will be controlled to fall continuously.

The opposite effect is observed when the operation is countercurrent. Thus, when the reaction is exothermic it is desirable, when conversion or product yield is to be maximized, to control the temperature profile so that it is continuously falling. When the reaction is endothermic it is important that the temperature profile continuously rise. For example, in the ammonia synthesis reaction where there is a balance between reaction equilibrium considerations and kinetic reaction rate, the temperature at the gas inlet port of the reactor should be relatively high to favor increased reaction rate, whereas a lower temperature is needed at the gas exit port of the reactor to promote ammonia conversion in view of equilibrium limitations. Thus, a temperature profile which is continually falling throughout the reaction will result in the highest conversion of hydrogen and nitrogen to ammonia.

While temperature profiles will vary with, e.g., reactor pressure and length as well as type of reaction, an optimal temperature profile for the solid and reaction fluid phases in ammonia synthesis may range from about 527° C. near the inlet port of the reactor to about 371° to 454° C. at the outlet port, assuming a maximum catalyst temperature of 527° C. Similar temperatures would apply to a hydrocarbon synthesis reaction by countercurrent methods, depending on the catalyst employed. The temperature range must be such as to preclude degradation of the catalyst and to maintain optimum product selectivity. The appropriate temperatures will also depend on the pressures employed, which may be up to about 40 atm or higher. An optimum temperature profile for hydrocarbon synthesis by cocurrent methods may vary from 310° to 350° C. at 25 atm depending on the catalyst. An optimal temperature profile for ethylene oxide synthesis will vary from about 225° to 275° C. for the entire reactor length to ensure greater than 75% selectivity and a sufficient reaction rate. The reaction temperature profiles for ammonia, hydrocarbon and ethylene oxide synthesis should be at or about, i.e., should substantially track, these optimum profiles.

The amount of deviation of the temperature profile from the optimum temperature profile for purposes of this invention will depend, for example, on the type of reaction, the length of the reactor, and the axial position in the reactor at which deviation occurs. The reaction temperature profile for ammonia synthesis should be within 30° C. of either side of the optimum temperature profile, and preferably within 5° to 10° C. of the optimum profile, except at the inlet portion of the reactor, which portion will vary with the length of the reactor. Thus, at the reaction fluid inlet section 22 of the ammonia synthesis reactor of FIG. 1, the deviation will be large as the reaction fluid is heated to the reaction initiation temperature. The deviation will decrease significantly as the fluid progresses up the reactor column. For ethylene oxide synthesis the deviation from the optimum temperature profile should be no greater than 50° C., preferably no greater than 20° C., of either side of the optimum temperature profile at any portion along the reactor, including the inlet and outlet zones. For hydrocarbon synthesis the deviation should be no greater than 20° to 30° C. of either side of the optimum temperature profile at all points along the reactor.

The relative rates at which the particles (solids) and reaction fluid are transported through the reactor will determine the temperature profile for the reaction. The benefit of the present invention is that the particles are circulated to a reaction zone without generally requiring an external regeneration or other treatment thereof. Through proper selection of the solids circulation rate, which may be expressed as a mass ratio of particles to reaction fluid throughout the reaction, which is a ratio of the weight per second of particles to the weight per second of reaction fluid flowing through the reactor, it is possible to cause the temperature profile along the length of the reactor to track very closely the optimum reaction temperature profile. The exact circulation rate to be employed will vary dramatically with the type of reaction utilized, the yield or conversion desired, and the reaction conditions. For example, in ammonia synthesis the mass ratio of solids to reaction fluid throughout the reaction will generally range from about 5:1 to 20:1, preferably 8:1 to 12:1, depending on, e.g., the operating conditions such as the outlet and inlet temperatures, the operating pressure, and the ammonia yield desired. In the epoxidation of ethylene the selectivity for epoxides increases with increasing rate of solids circulation for a given production rate of epoxide. But at a given solids circulation rate, increasing the degree of conversion to increase production rates results in decreased selectivity. It is also noted that as the circulation rate increases, the rise in temperature profile decreases. Generally, the solids-to-reaction fluid mass ratio for epoxidation, and hydrocarbon synthesis as well, may range from 5:1 to 1000:1, preferably 15:1 to 50:1.

It is noted that the practitioner, by routine testing, will be able to determine what variations and experimentation would be required to obtain maximum selectivity, conversion and/or product yield for a given reaction at each point along the reactor. For example, use of computer simulation techniques is well known in the art for predicting optimum conditions given specific values for relevant reaction parameters. Such mathematical simulations are described for multistage ammonia reactors in, e.g., D. Gelbin, *Chem. Eng. Prog. Symp. Series*, 60, 41 (1964) and M. Shah, *Ind. and Eng. Chem.*, 59, 72 (1967). In addition, L. Shipmen et al., *Chem. Eng. Prog.*, 64, 59 (1968) describes various reaction parameters to optimize design of ammonia quench converters. As to ethylene oxidation, a reference for the kinetics used in computer simulations is R. E. Kenson et al., *J. Phys. Chem.*, 74, 1493 (1970).

In an exothermic reaction the heat evolved is carried off by the particles phase or reaction fluid phase, which is in turn cooled externally from the reactor. In an endothermic reaction the heat required for reaction is supplied externally to the entering solids or reaction fluid. In a countercurrent operation for an exothermic reaction, for example, it may be possible to adjust conditions such that the heat content of the solids leaving the reactor will equal the heat content of the solids entering the reactor. In that case, the solids may be recirculated with no external heat exchange, and the heat generated by the reaction will leave the reactor by means of the reaction fluid phase. This is desirable because it is easier to dispose of the generated heat when it is contained in the fluid phase from which it can be recovered in the form of steam or used to reheat the feed gas entering the reactor in a continuous operation. If a large portion of the heat is contained in the solids phase as it exits from the reactor, the solids must be recirculated in a heat exchanger where a coolant is circulated to absorb the heat evolved.

The process herein may be carried out in a batch operation but is preferably conducted using a continuous mode whereby the solids are regenerated, as by conditioning or reconditioning, and recycled, optionally through a header, and the feed gas of reaction fluid is continuously pumped to the reactor while the exit gas is treated so as to remove the reactant gases and recover the product. Typically, the ammonia is recovered by cooling the reactant gases to condense ammonia, and the unreacted hydrogen and nitrogen gases are recirculated, reheated and mixed with fresh feed gas, and returned to the reactor. Any inert gas may be used to cool the solids or to assist in elevating them to the header as necessary.

The examples which follow will illustrate the features of the present invention. Unless otherwise indicated all parts and percentages are given by weight. It is noted that all of the following examples are based on mathematical calculations assuming the given reaction parameters.

EXAMPLE I

Temperature-Controlled Reactor for Ammonia Synthesis

Ammonia is synthesized from hydrogen and nitrogen using the reactor depicted in FIG. 1. A feedstream mixture comprised of 71.4% hydrogen, 23.8% nitrogen and 4.8% ammonia by moles is transported at about 229° C. and 2200 psia (149.8 atm) at a rate of 60 kg per second through line 10 to the inlet port 12 at the bottom of a vertical reactor 14 having a length of 20 feet (6 m) which is subjected to a magnetic field provided by electrical coils 16. At the same time iron particles having a particle size of about 200 microns in diameter are transported via line 18 at a rate of 672 kg per second (to yield a particles to gas mass ratio for the reactor of 11.2:1) to the solids inlet port 20 at the top of reactor 14 so that the particles are fluidized in the reactor by the upward flowing gas. As the gas mixture flows up the reactor column it is heated in section 22 of the reactor to the reaction initiation temperature of 343° C. by contact with the hotter descending iron particles. The reaction then proceeds rapidly as the heat from the reaction is evolved, thereby increasing the temperature in section 24 of the reactor to a maximum reaction temperature of 527° C. This heat is removed from the gas stream by the cold catalyst particles flowing downward through the reactor which are absorbing heat in section 26 of the reactor from the gas stream. As the gas stream cools, further reaction occurs as the equilibrium favors a higher ammonia concentration in the gas stream. The gas stream exits from the reactor through the top via line 28 at about 435° C. which is a temperature level close to the optimum temperature for maximizing utilization of catalyst (maximizing reaction rate) at that condition of gas composition. The gas, containing a high concentration of ammonia, is further carried to a cooling chamber (not shown) in which the ammonia is condensed and the unreacted nitrogen and hydrogen reactant gases are recirculated, reheated, mixed with feed gas and returned to the reactor. The yield of ammonia is 21.6% by weight. Meanwhile, catalyst particles in the upper portion of the reactor, which have been heated by the exiting gas, descend through the reactor and are cooled as the gas is being heated. When the solids finally exit through the reactor via outlet 30, they are at a temperature of about 435° C. and are recirculated to the top of the reactor in a continuous operation by the gas, which bypasses the reactor and carries the solids via line 18 to the inlet port 20 and returns to the reactor via line 32.

Figure 2:
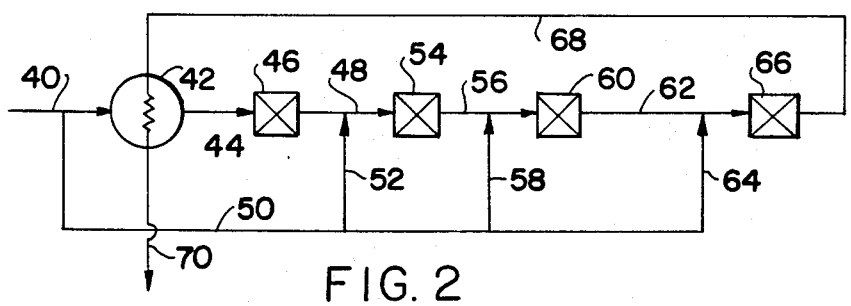
FIG. 2 represents a schematic flow diagram, for comparative purposes, of an ammonia synthesis process utilizing a conventional stagewise four-bed adiabatic reactor equipped with inter-bed quench for cooling between the beds.

In a comparative example a conventional four-bed adiabatic reactor with quench cooling between the beds as depicted in FIG. 2 is employed to synthesize ammonia. The feedstream mixture described above is passed, at a rate of 60 kg per second, through line 40 to a preheater 42 which heats the mixture to about 427° C. The mixture is then passed through line 44 to a fixed catalyst bed 46 containing iron particles and is exited through line 48, whereupon it is cooled with the quenching initial gas mixture passing through line 50 to line 52. On cooling, the feedstream mixture is introduced into fixed catalyst bed 54 containing iron particles and is exited through line 56 and cooled by the quenching gas from line 58. The thus-cooled gaseous mixture is then passed through fixed catalyst bed 60 containing iron particles and exited via line 62 where it is quenched with inlet gas from line 64. The stream is then passed through the fourth fixed catalyst bed 66 containing iron particles from whence it exits via line 68 and is circulated to the preheater to exchange its heat and the cooled gas is then transported via line 70 to a cooling chamber (not shown) in which the ammonia gas is condensed and the unreacted reactant gases are recirculated to the reactor as described above.

Figure 3:
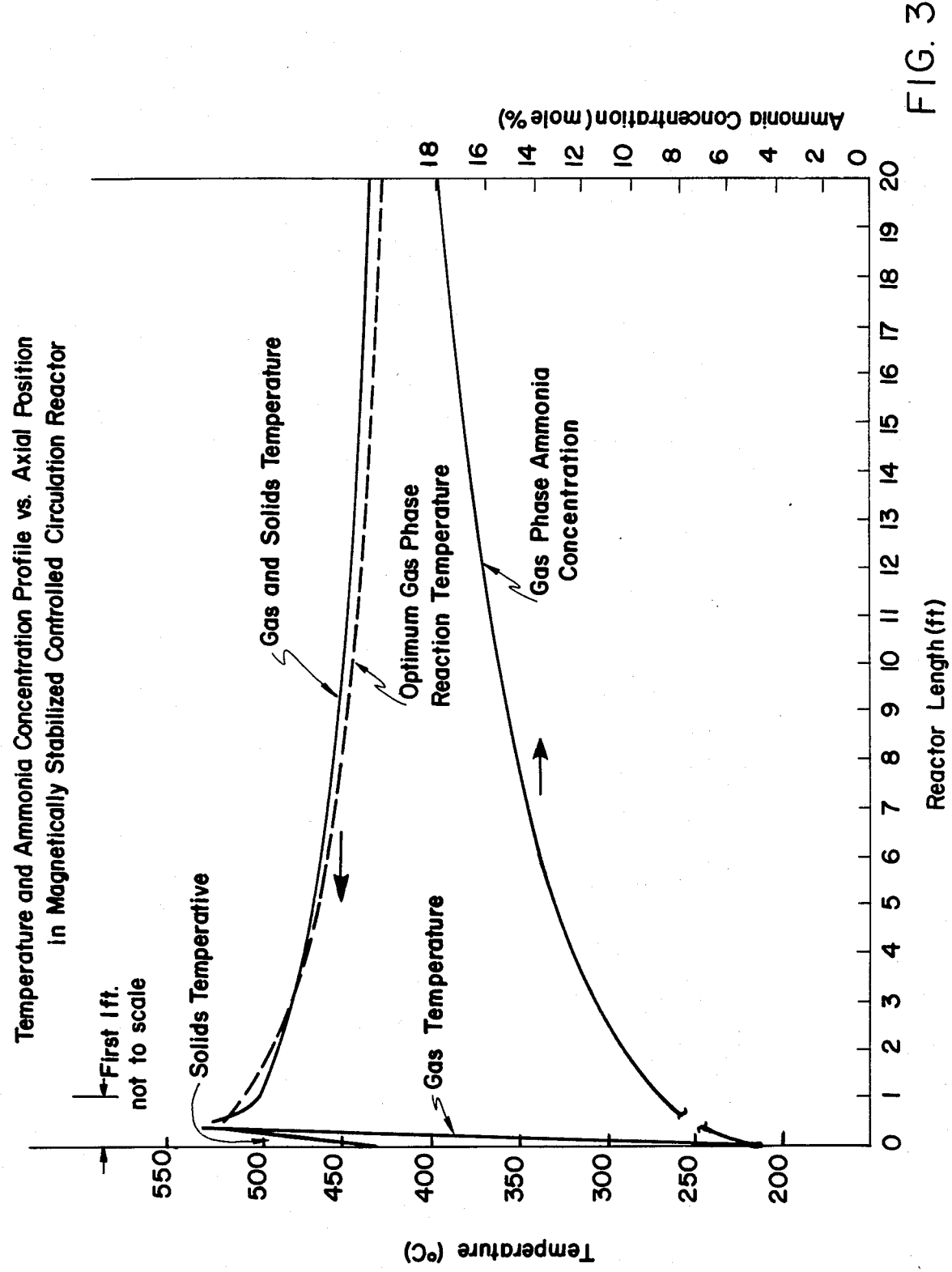
FIG. 3 represents a graphical illustration of the temperatures of the solids and gas phases as a function of the axial position in the reactor (temperature profile) achieved in an ammonia synthesis process under conditions using the reactor of FIG. 1.
Figure 4:
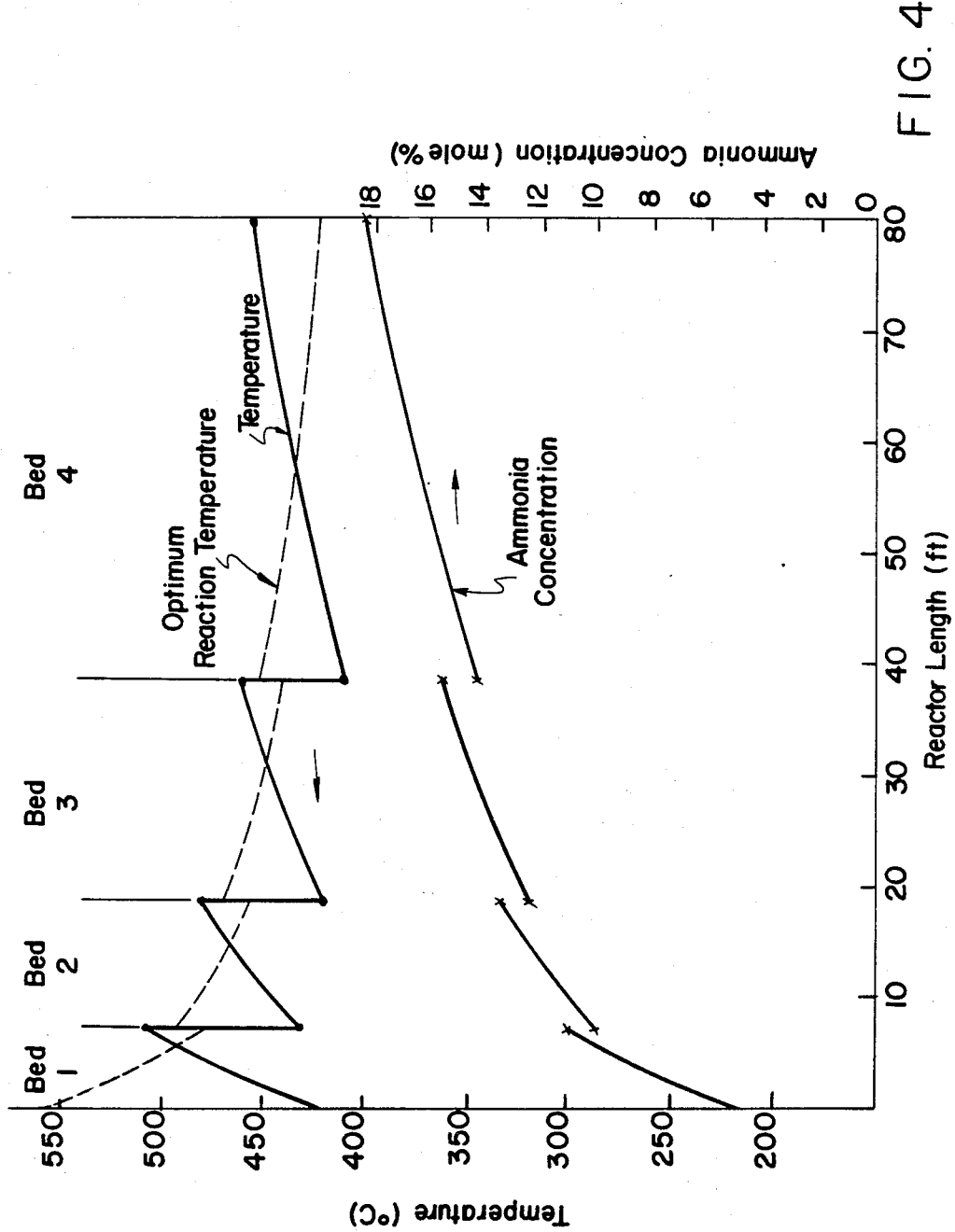
FIG. 4 represents a graphical illustration of the temperature profile and ammonia concentration in each bed of the comparative four-bed reactor of FIG. 2 as a function of the axial position in the reactor. It also illustrates the optimum reaction temperature, which is a function of the ammonia concentration, along the length of the reactor.

FIGS. 3 and 4 respectively depict the results observed for the actual reaction temperature profiles and the optimum temperature profiles (for maximum reaction rate, which is a function of ammonia concentration) using the reactor of FIG. 1 representing this invention and the comparative fixed bed reactor of FIG. 2.

FIG. 3 illustrates the solids and gas phase temperature profile and gas phase ammonia concentration profile along the length of the reactor of FIG. 1. The colder inlet gas is rapidly heated by the hotter solids to the reaction temperature (343° C.) and beyond, resulting in the attainment of the peak temperature (527° C.) within the first one foot (30 cm) of reactor length (which first foot is not drawn to scale on the abscissa of the FIG. 3 plot). As the gas phase proceeds along the length of the reactor, the recirculated solids cool the gas and further ammonia conversion takes place.

FIG. 3 demonstrates the improved utilization of catalyst versus utilization of the same type of catalyst in a conventional fixed bed reactor. Thus, in FIG. 3 the plot of gas phase temperature parallels the plot of the optimum reaction temperature along the length of the reactor, whereas in FIG. 4 a major portion of the reaction in the conventional four-bed adiabatic reactor of FIG. 2 with quench cooling operates far from the optimum reaction temperature profile. The beneficial effect of the process of this invention can also be seen from the lower amount of catalyst volume required using the reactor in FIG. 1 to achieve the same conversion level as achieved using higher catalyst volumes in the conventional reactor in FIG. 2. At a solids to gas mass ratio of 11.2:1, the catalyst volume required using the process herein is only 40% of the volume required using the conventional reactor, and only 3% more than the ideal minimum catalyst volume required if the optimum temperature profile could be reproduced exactly.

It is noted that FIG. 3 is based on a solids to gas mass flow ratio of 11.2:1 and a gas inlet temperature of 213° C., resulting in a gas temperature no more than 8° C. different from the optimum temperature throughout all but the first one foot of the reactor. Under the same operating conditions, solids to gas mass flow ratios of 9.8:1 to 11.5:1 achieve similar levels of ammonia synthesis, but a ratio of 8.2:1 or lower does not provide as efficient a level of performance as that shown in FIG. 3, with a ratio of 8.2:1 operating as much as 27°-32° C. from the optimum temperature near the reactor outlet. By separate calculations it is shown that the solids to gas mass ratio can be adjusted to maintain a close approach to the optimum temperature profile if different process conditions are employed to synthesize the ammonia.

Ammonia yields higher than the 21.6% yields obtained using the above processes can be obtained by operating at a lower gas phase outlet temperature and by varying the gas inlet temperature, solids to gas mass ratio and reactor length. The consequently higher catalyst volume required to obtain the higher yield will still be less than that volume required using a conventional fixed reactor to obtain the same higher yield. Thus, in process designs where yield is to be maximized, such as in synthesis loop designs employing lower pressures than the 2200 psia (149.8 atm) employed in the above example, a reactor of the type depicted in FIG. 1 may be particularly advantageous.

EXAMPLE II

Controlled Circulation Rate for Ethylene Oxide Synthesis

In a cocurrent operation represented by FIG. 5 a feed gas mixture consisting of 0.079, 0.079 and 0.842 mole fraction of ethylene, oxygen and nitrogen gas, respectively, is passed through line 80 into the bottom of a reactor column 82 having a length of 2-3 feet (61-92 cm) surrounded by a coiled electromagnet 84 which provides a magnetic field strength of 25-250 oersted. Cocurrently with the entry of the feed gas, solid silver-coated, spherical particles having a diameter of 180 microns, a particle density of 3.97 $g/cm^3$ and a specific heat of 0.2 cal/g° C. are entered at a rate of 5 cm/sec (to yield a particles to gas mass ratio of 20:1) via line 86 to the reactor. The temperature of both the inlet gas and the inlet solids is 225° C., the inlet pressure of the gas is 31.74 atm, and the superficial gas velocity is 16.4 cm/sec. The temperatures of the solid and gas phases in the reactor differ by less than 0.1° C. The solids exit from the top of the reactor via line 88 to a chamber 90 through which recirculating cool gas from the feed gas is passed via line 92. The hot feed gas from the exchange exits chamber 90 via line 94 and is passed through a heat exchanger 96 to be recirculated to the chamber to cool the solids and elevate them via lines 92 and 98 to the solids header 100. The solids from the header are then transported to the bottom of the reactor via line 86. In the meantime, the feed gas from the reactor is exited through line 87 to a further operation (not shown) wherein the ethylene oxide is separated from the other components in the gas. The ethylene oxide is obtained in a yield of 70-80% by weight of the maximum yield possible.

Figure 6:
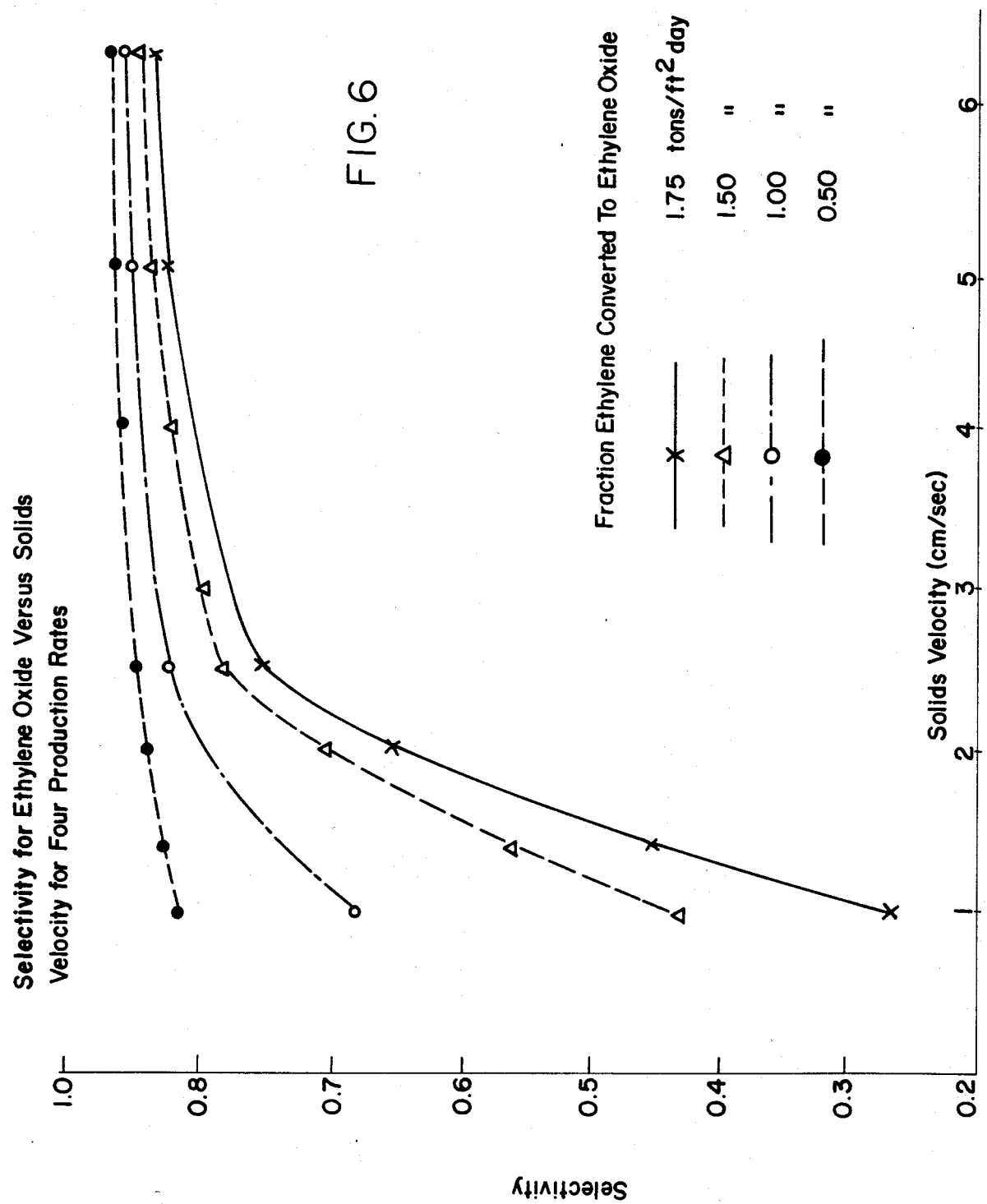
FIG. 6 represents a graphical illustration of the selectivity for ethylene oxide as a function of solids velocity for four given production rates.

FIG. 6 depicts the effect on selectivity for ethylene oxide (defined as the fraction of ethylene converted to ethylene oxide) of increasing solids velocity (maintaining the same gas velocity and other conditions throughout) for four given production rates of ethylene oxide ranging from 0.50 to 1.75 tons per square feet per day. It can be seen that selectivity increases with increasing solids velocity (and thus increasing flux of solids heat capacity) for a given production rate.

Figure 7:
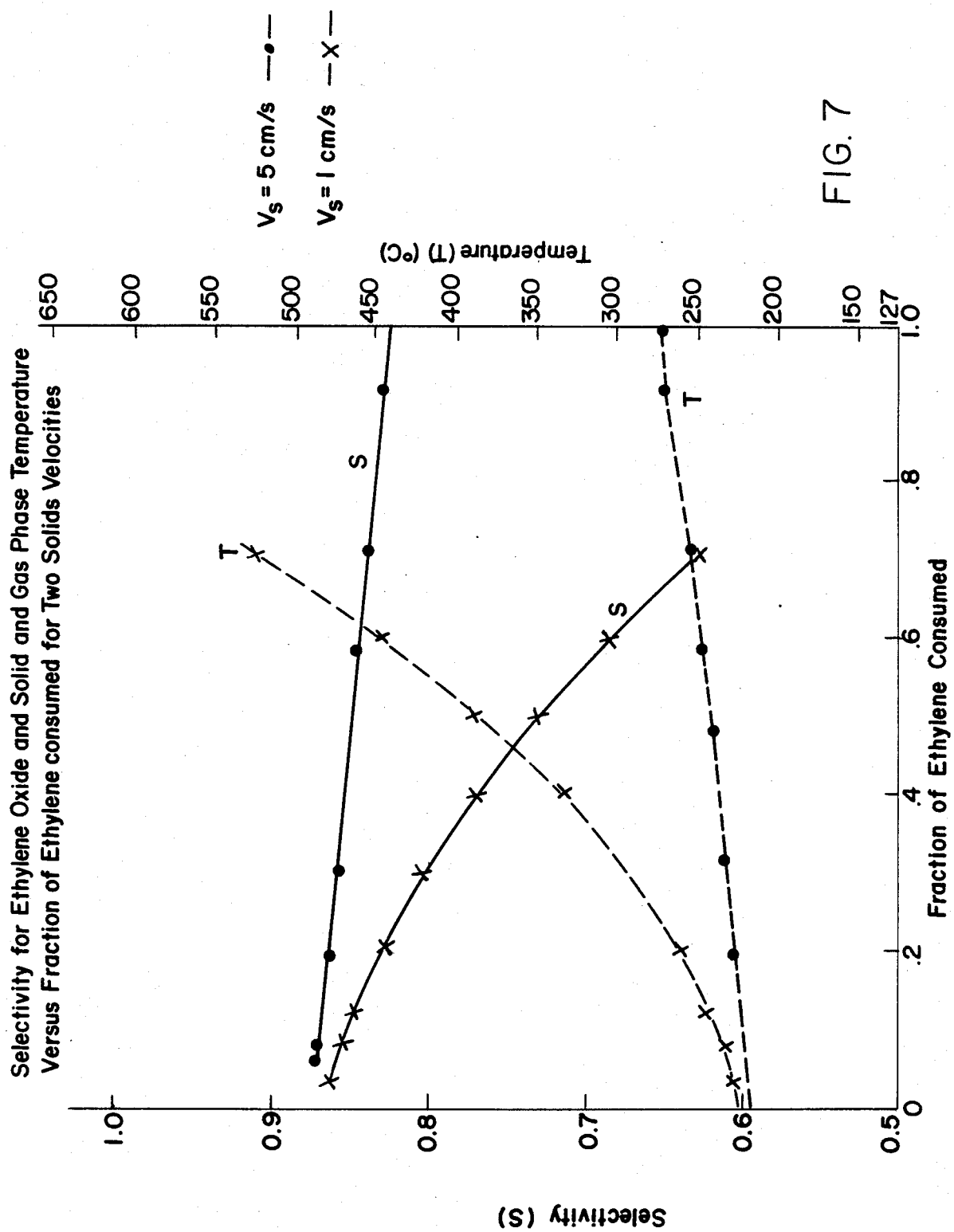
FIG. 7 represents a graphical illustration of the solids and gas temperature (temperature profile) in the reactor and the selectivity for ethylene oxide as a function of ethylene consumed for two solids velocities.

FIG. 7 depicts the effect on the solids and gas temperature profile (T) in the reactor and the effect on the selectivity for ethylene oxide (S) as the reaction proceeds for two rates of solids velocity, i.e., 1.0 cm/sec (solids to gas mass ratio of 4:1) and 5.0 cm/sec (solids to gas mass ratio of 20:1), maintaining other conditions constant. It can been seen that the 5.0 cm/sec. rate stabilizes both the selectivity at greater than 80% levels and the reaction temperature profile in the 225°-277° C. range. This is believed to be due to the increased heat capacity provided by the flowing solids, which reduces longitudinal exotherms to achieve acceptable selectivity levels. The corresponding conversion of ethylene exceeds 50%.

FIG. 8 depicts the effect of decreasing the inlet temperature from 225° C. to 200° C. and of increasing the solids velocity from 1 to 5 cm/sec. (maintaining other conditions constant) on the length of the reactor required to achieve an ethylene oxide production rate of

EXAMPLE III

Controlled Circulation Rate for Hydrocarbon Synthesis

The procedure of Example II is repeated using a feed gas mixture consisting of 0.14 and 0.86 mole fraction of carbon monoxide and hydrogen, respectively, and a potassium-promoted, fused iron catalyst having a diameter of 200 microns. The solids to gas mass ratio for the reaction is 200:1 and the inlet and outlet temperatures of the gas are 310° and 340° C., respectively. The pressure of the system is 25 atm. At least 80% of the carbon monoxide is converted to olefins, alkanes, oxygenated hydrocarbons, aromatic compounds and carbon dioxide.

The maximum temperature reached will not exceed 350° C., as the solids provide sufficient heat capacity. Thus, the catalyst is protected from deactivation by excessive temperatures. The movement of the catalyst into and from the reactor in a plug-flow manner also gives a narrow residence time distribution for better control of selectivity and allows removal of coke deposits from the catalyst.

In summary, the present invention is seen to provide an improved process for conducting an endothermic or exothermic reaction under fluidization conditions whereby the reaction fluid and a bed of flowable particles are transported at relative rates so as to approach an optimum temperature profile for the particular reaction involved to maintain both conversion and selectivity at high levels so as to maximize product yield per pass and reduce or eliminate recycle.

What is claimed is:

1. A process for conducting an endothermic or exothermic chemical reaction in a reactor comprising:
    (a) subjecting a flowable bed containing magnetizable particles to an applied magnetic field having a substantial component along the direction of the external force field within the bed;
    (b) circulating a reaction fluid through the reactor in a plug-flow manner at a rate such that the fluid exerts pressure against and levitates the particles in the bed and under conditions such that an endothermic or exothermic reaction takes place in the presence of the bed;
    (c) circulating the bed of particles through the reactor in a plug-flow manner, and after its exit from the reactor, recirculating the bed to the reactor, the circulating and recirculating of the bed being conducted at a rate such that the temperature profile of the bed and reaction fluid throughout the entire contact of the bed with the reaction fluid is at or about the temperature profile which results in maximization, at each position in the reactor, of at least one of the following: conversion, selectivity or product yield; and
    (d) recovering one or more reaction products.

2. The process of claim 1 wherein the particles are circulated in a direction which is countercurrent to the direction of passage of the reaction fluid.

3. The process of claim 1 wherein the particles are circulated in a direction which is cocurrent with the direction of passage of the reaction fluid.

4. The process of claim 1 wherein the particles are catalytic solids and the reaction is exothermic.

5. The process of claim 2 wherein the reaction is the synthesis of ammonia.

6. The process of claim 3 wherein the reaction is the epoxidation of ethylene.

7. The process of claim 1 which is conducted in a batch operation.

8. The process of claim 1 which is conducted in a continuous operation.

9. The process of claim 1 wherein the temperature profile is continuously falling or rising throughout the reaction.

10. The process of claim 5 wherein the temperature profile is continuously falling throughout the reaction such that product yield is maximized.

11. The process of claim 10 wherein the rate of circulating and recirculating the bed is such that the mass ratio of the particles to the reaction fluid throughout the reaction is from 5:1 to 20:1.

12. The process of claim 6 wherein the temperature profile is continuously rising throughout the reaction such that conversion or selectivity or both are maximized.

13. The process of claim 12 wherein the temperature profile is maintained throughout the reaction at below about 277° C.

14. The process of claim 12 wherein the rate of circulating and recirculating the bed is such that the mass ratio of the particles to the reaction fluid throughout the reaction is from 5:1 to 1000:1.

15. A continuous process for conducting the synthesis of ammonia in a reactor comprising:
    (a) subjecting at least a portion of a flowable bed containing magnetizable catalytic particles to an applied magnetic field having a substantial component along the direction of the external force field within the bed;
    (b) circulating a reaction fluid consisting of hydrogen, nitrogen and ammonia through the reactor in a plug-flow manner at a rate such that the fluid exerts pressure against and levitates the particles in the bed and under conditions such that an exothermic reaction takes place in the presence of the bed;
    (c) circulating the bed of particles through the reactor in a plug-flow manner and after its exit from the reactor recirculating the bed to the reactor, the circulating and recirculating of the bed being conducted at a rate such that the temperature profile of the bed and reaction fluid throughout the entire contact of the bed with the reaction fluid is continuously falling and is at or about the temperature profile which results in maximization, at each position in the reactor, of product yield, and at a rate such that the mass ratio of the particles to the reaction fluid throughout the reaction is from 5:1 to 20:1; and
    (d) recovering ammonia as a product.

16. A continuous process for conducting the synthesis of ethylene oxide in a reactor comprising:
    (a) subjecting at least a portion of a flowable bed containing magnetizable catalytic particles to an applied magnetic field having a substantial component along the direction of the external force field within the bed;
    (b) circulating a reaction fluid consisting of a mixture of ethylene, oxygen and nitrogen through the reactor in a plug-flow manner at a rate such that the fluid exerts pressure against and levitates the particles in the bed and under conditions such that an exothermic reaction takes place in the presence of the bed;

(c) circulating the bed of particles through the reactor in a plug-flow manner and after its exit from the reactor recirculating the bed to the reactor, the circulating and recirculating of the bed being conducted at a rate such that the temperature profile of the bed and reaction fluid throughout the entire contact of the bed with the reaction fluid is continuously rising but is kept below about 277° C. and is at or about the temperature profile which results in maximization, at each position in the reactor, of conversion or selectivity or both, and at a rate such that the mass ratio of the particles to the reaction fluid throughout the reaction is from 5:1 to 1000:1; and (d) recovering ethylene oxide as a product.

* * * * *